United States Patent [19]

Shroff et al.

[11] 4,302,591
[45] Nov. 24, 1981

[54] ANTIHYPERTENSIVE AMINES

[75] Inventors: James R. Shroff, Riverside, Conn.; Bernard Loev, Scarsdale, N.Y.

[73] Assignee: USV Pharmaceutical Corporation, Tuckahoe, N.Y.

[21] Appl. No.: 182,885

[22] Filed: Sep. 2, 1980

[51] Int. Cl.³ .............. C07D 401/04; C07D 401/14; C07D 211/82
[52] U.S. Cl. .................... 546/257; 546/256; 546/258; 546/271; 546/330; 546/333; 546/286; 546/287; 546/315; 546/316; 546/318; 546/321
[58] Field of Search .............. 546/257, 256, 258, 321, 546/270, 287, 316, 315, 271, 330, 333, 286, 287; 424/266

[56] References Cited

FOREIGN PATENT DOCUMENTS 48-8124 1/1973 Japan .................... 546/321
7010860 1/1971 Netherlands .................... 546/321

Primary Examiner—John M. Ford
Attorney, Agent, or Firm—Gilbert W. Rudman; Leon E. Tenenbaum; Ernest B. Lipscomb, III

[57] ABSTRACT

Iminobenzyl dihydropyridines of the formula

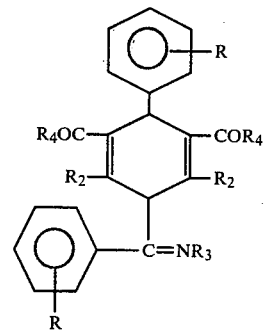

wherein,
each R is alkyl, alkenyl, alkynyl, cycloalkyl, aryl, aralkyl, sulfonamido, halogen, alkoxy, alkenyloxy, alkynyloxy, cyano, hydroxy, acyloxy, nitro, amino, alkylmercapto, alkylamino, alkanoylamino, carbalkoxyamino, carboxy, methanesulfonyl, carbalkoxy or trifluoromethyl;
each $R_4$ is lower alkoxy;
each $R_2$ is lower alkyl;
and $R_3$ is alkyl, alkenyl, alkynyl, cycloalkyl, heterocyclic or

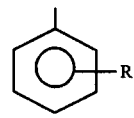

wherein R is as previously defined; have anti-hypertensive activity.

19 Claims, No Drawings

ANTIHYPERTENSIVE AMINES

This invention relates to new anti-hypertensive agents and more particularly to certain new substituted 1,4-dihydropyridines possessing useful anti-hypertensive activity.

Substituted 1,4-dihydropyridines are known and have been described in the literature as vasodilating agents. 1,4-Dihydropyridines having vasodilating activity are characterized by the presence of alkyl substituents in the 2 and 6 positions of the pyridine ring and carbalkoxy groups in the 3,5-positions usually with a substituent, most commonly phenyl or substituted phenyl, in the 4-position. To increase the water-solubility of these compounds, M. Iwanami, et al. Chem. Pharm. Bull. 27 (6) 1426–1440 (1979) described the effect of N-substitution of the pyridine ring nitrogen with, inter alia, aminoalkylene groups such as pyrollidinoethyl and dimethylaminoethyl. Thus, water-solubility determinations with compounds such as diethyl 1,4-dihydro-4-(3-nitrophenyl)-2,6-dimethyl-1-(2-dimethylaminoethyl) compound were determined as was the potency thereof as vasolidilators but these compounds were determined to be of lower potency than known compounds such as the corresponding 1-ethoxymethyl compound.

Japanese patent specification No. 70767/76 describes as anti-hypertensive and vasodilating agents 1,4-dihydropyridines of the formula

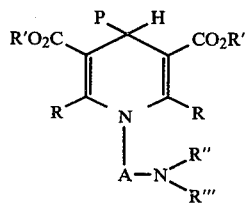

in which R is alkyl; P is substituted (mono or di-) phenyl, pyridyl, furyl, or thienyl in which the substituents are H, halogen, —CN, —NO$_2$, —NH$_2$, —N(CH$_3$)$_2$, carboxyl, methoxy, ethoxy, butoxy, sulfonyl, methylsulfonyl or acetyl; R' is alkyl, aralkyl, methyl, ethyl, isopropyl, t-butyl, ethoxyethyl, benzyl, phenethyl, or 4-methoxybenzyl; A is alkylene; and R" and R''' are each alkyl and, when taken together, form a pyrollidine ring with the N to which they are attached.

The new compounds of the present invention are N-iminobenzyl-dihydropyridines of the formula:

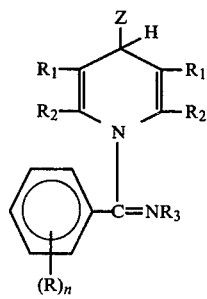

FORMULA I wherein
Z is

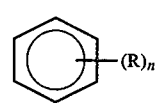

,
cycloalkyl, or heterocyclic wherein R and "n" are as defined herein;

each R is hydrogen, alkyl, alkenyl, alkynyl, cycloalkyl, aryl, aralkyl, sulfonamido, halogen, alkoxy, alkenyloxy, alkynyloxy, cyano, hydroxy, acyloxy, nitro, amino, alkylmercapto, alkylamino, alkanoylamino, carbalkoxyamino, carboxy, methanesulfonyl, carbalkoxy or trifluoromethyl and two R groups, when taken together, form a methylenedioxy;

each R$_1$ is cyano or COR$_4$ wherein R$_4$ is hydroxy, alkoxy, alkyl, alkenyl, alkynyl, alkylamino, amino, cycloalkyl, or alkoxyalkoxy;

each R$_2$ and R$_3$ are alkyl, alkenyl, alkynyl, cycloalkyl, heterocyclic or

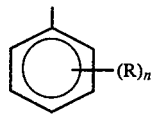

wherein R and "n" are as defined herein;
and N=0–3;
and acid addition salts thereof.

The total number of carbon atoms in each such hydrocarbyl substituent can range up to about 10.

Heteroaryl as employed herein refers to any heterocyclic structure in which at least one of O, S and N are present as the hetero atoms. These include thiophene, furan, pyridine, thiazole, pyrimidine, pyrrole, benzofuran, quinoline, benzothiophene and substituted heterocycles.

The preferred compounds are those in which the hydrocarbyl radicals contain up to about 7 carbon atoms when aliphatic and up to about 10 carbon atoms when aromatic, e.g., phenyl, tolyl and naphthyl.

The particularly preferred compounds of the invention are compounds of Formula II:

FORMULA II

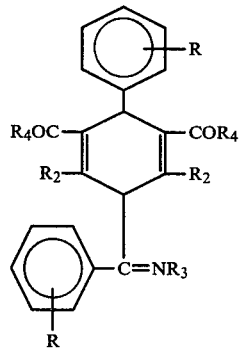

in which each R$_4$ is lower alkoxy, each R$_2$ is lower alkyl and R and R$_3$ are as previously defined herein.

The new compounds of the invention can be prepared by art-recognized procedures from known starting compounds as described, for example, in the literature hereinbefore described. The following procedure constitutes a particularly convenient preparative method:

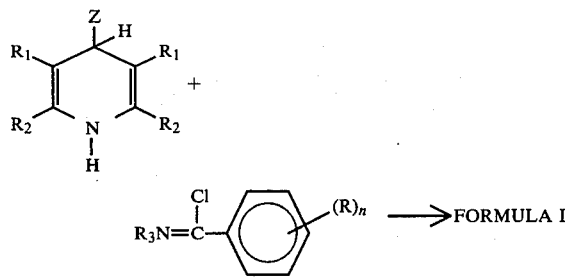

The reaction can be carried out in a solvent in the presence of sodium hydride, or any alkali metal hydride or alkoxide as is commonly employed in condensation reactions. The reaction is effected in two steps, the first metallation with the alkali metal compound, and the second, condensation with the halide, "X", containing compound, which is usually chloride. The hydrides are convenient since the progress of the metallation reaction can be followed by observing the evolution of hydrogen gas. The metallation step is normally carried out at room temperature. The reaction mixture thereafter is heated at elevated temperature, e.g. at steam bath temperature at or about 100° C., or above up to about 150° C. depending on the boiling point of the selected solvent, and the halide compound is then added, usually in controlled amounts in dropwise fashion and, after addition is completed, the reaction mixture is digested by heating at the elevated temperature.

The solvent employed in the reaction can be any of a wide variety of organic solvents for the reacting compounds including dimethylformamide, dioxane, tetrahydrofuran, lower alkanones, such as acetone, methyl isobutyl ketone, and the like. The solvent should not react with the reacting materials or the alkali metal compound selected and is preferably low boiling to permit easy recovery of product.

The product is obtained in the usual fashion, as by cooling to cause precipitation or evaporation of the solvent to obtain the product as a residue.

Employing this procedure, a variety of new iminobenzyl-1,4-dihydropyridines of FORMULA II can be prepared:

| $R_1$ | $R_2$ | R | n |
|---|---|---|---|
| $CH_3$ | $C_2H_5$ | H | |
| $CH_3$ | $C_2H_5$ | $CH_3$ | 1 |
| $CH_3$ | $C_2H_5$ | H | 1 |
| $C_2H_5$ | $C_2H_5$ | Cl | 1 |
| $CH_3$ | $1\text{-}C_3H_7$ | CN | 1 |
| $CH_3$ | $C_2H_5$ | $NO_2$ | 1 |
| $CH_3$ | $C_2H_5$ | OH | 1 |
| $C_3H_7$ | $CH_3$ | $CF_3$ | 1 |
| $C_4H_9$ | $C_2H_5$ | $OCH_3$ | 1 |
| $C_6H_{13}$ | $C_2H_5$ | COOH | 1 |
| $i\text{-}C_4H_9$ | $CH_3$ | $OCH_3$ | 1 |
| $CH_3$ | $C_2H_5$ | $OCH_3$ | 2 |
| $CH_3$ | $C_2H_5$ | $CH_3$ | 2 |
| $CH_3$ | $C_2H_5$ | $CH_2C_6H_5$ | 1 |
| $CH_3$ | $C_2H_5$ | $C(CH_3)_3$ | 1 |
| $CH_3$ | $C_2H_5$ | $C_6H_5$ | 1 |
| $CH_3$ | $C_2H_5$ | H | |
| $CH_3$ | $C_2H_5$ | Cl | 3 |
| $CH_3$ | $C_2H_5$ | Cl | 2 |
| $CH_3$ | $C_2H_5$ | Cl | 2 |
| $CH_3$ | $C_2H_5$ | $CH_2=CH-CH_2$ | 1 |
| $CH_3$ | $C_2H_5$ | H | |

-continued

| $R_1$ | $R_2$ | R | n |
|---|---|---|---|
| $CH_3$ | $C_2H_5$ | $CH_3$ | 1 |
| $CH_3$ | $C_2H_5$ | H | |
| $CH_3$ | $C_2H_5$ | H | |
| $CH_3$ | $C_2H_5$ | $CH_3$ | 1 |
| $CH_3$ | $C_2H_5$ | $CH_3$ | 2 |
| $CH_3$ | $C_2H_5$ | H | |
| $CH_3$ | $C_2H_5$ | H | |
| $CH_3$ | $C_2H_5$ | $CH_3$ | 1 |
| $CH_3$ | $C_2H_5$ | Cl | 1 |
| $CH_3$ | $C_2H_5$ | CN | 1 |
| $CH_3$ | $C_2H_5$ | $NO_2$ | 1 |
| $CH_3$ | $C_2H_5$ | OH | 1 |
| $CH_3$ | $C_2H_5$ | $CF_3$ | 1 |
| $CH_3$ | $C_2H_5$ | $OCH_3$ | 1 |
| $CH_3$ | $C_2H_5$ | COOH | 1 |
| $CH_3$ | $C_2H_5$ | $OCH_3$ | 1 |
| $CH_3$ | $C_2H_5$ | $OCH_3$ | 2 |
| $CH_3$ | $C_2H_5$ | $OCH_3$ | 1 |
| $CH_3$ | $C_2H_5$ | $CH_2=CH-CH_2-$ | 1 |
| $CH_3$ | $C_2H_5$ | $COOCH_3$ | 1 |
| $CH_3$ | $C_2H_5$ | $COOCH_3$ | 1 |
| $CH_3$ | $C_2H_5$ | $NH_2$ | 1 |

The present new heterocyclic compounds are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, succinic, arylsulfonic, e.g. p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds are particularly useful as anti-hypertensive agents. The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other antihypertensive agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

Diethyl 1,4-dihydro-1-(N-methylbenzimidoyl)-2,6-dimethyl-4-2-trifluoromethylphenyl)-3,5-pyridine dicarboxylate To a slurry of sodium hydride (1.8 g., 37.5 mmole, 50:50 oil dispersion) in dry DMF (50 ml.) under nitrogen atmosphere was added a solution of diethyl-1,4-dihydro-4-(2-trifluoromethylphenyl)-2,6-dimethyl-3,5-pyridine dicarboxylate (14.5 g., 36.5 mmole) in DMF (150 ml.). A gas bubbler was attached, the nitrogen flow discontinued and the mixture was warmed in a water bath until bubbling ceased. The system was again placed under nitrogen and solution of N-methylbenzimidoyl chloride (5.6 g., 36.5 mmole) in DMF (200 ml.) was added slowly. The reaction mixture was refluxed for a period of 18 hours, allowed to cool and vacuum filtered. The filtrate was evaporated in vacuo to a viscous oil which was extracted in refluxing hexane, leaving a black oily residue. The crude product crystallized from the hexane solution and was recrystallized from hexane (1.0 g., 5.3%).

EXAMPLE 2

Diethyl 1,4-dihydro-1-(N-isobutylbenzimidoyl)-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)-2,6-dimethyl-3,5-pyridine dicarboxylate and N-isobutyl-benzimidoyl chloride (0.5 g., 6.9%).

EXAMPLE 3

Diethyl 1,4-dihydro-1-(N-cyclohexylbenzimidoyl)-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)-2,6-dimethyl-3,5-pyridine dicarboxylate and N-cyclohexylbenzimidoyl chloride (10.1 g., 45.9%).

EXAMPLE 4

Diethyl 1,4-dihydro-1-(N-ethylbenzimidoyl)-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)2,6-dimethyl-3,5-pyridine dicarboxylate and N-ethyl benzimidoyl chloride (1.6 g., 8.0%).

EXAMPLE 5

Diethyl 1,4-dihydro-[N-(4-fluorophenyl)benzimidoyl]-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)-2,6-dimethyl-3,5-pyridine dicarboxylate and N-(4-fluorophenyl)benzimidoyl chloride (4.0 g., 17.8%).

EXAMPLE 6

Diethyl 1,4-dihydro-1-(N-propylbenzimidoyl)-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)2,6-dimethyl-3,5-pyridine dicarboxylate and N-propylbenzimidoyl chloride (5.6 g., 20.6%).

EXAMPLE 7

Diethyl 1,4-dihydro-1-(N-neopentylbenzimidoyl)-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)-2,6-dimethyl-3,5-pyridine dicarboxylate and N-neopentylbenzimidoyl chloride (3.3 g., 11.5%).

EXAMPLE 8

Diethyl 1,4-dihydro-1-(N-phenylbenzimidoyl)-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)-2,6-dimethyl-3,5-pyridine dicarboxylate and N-phenylbenzimidoyl chloride (1,3 g., 9.0%).

EXAMPLE 9

Diethyl 1,4-dihydro-1-(N-methylbenzimidoyl)-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)-2,6-dimethyl-3,5-pyridine dicarboxylate and N-methylbenzimidoyl chloride (1.0 g., 5.3%).

EXAMPLE 10

Diethyl 1,4-dihydro-1-[N-(2-trifluoromethylphenyl)benzimidoyl]-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)-2,6-dimethyl-3,5-pyridine dicarboxylate and N-(2-trifluoromethylphenyl)benzimidoyl chloride (3.3 g., 21.0%).

EXAMPLE 11

Diethyl 1,4-dihydro-1-[N-(2-methoxyphenylbenzimidoyl]-2,6-dimethyl-4-(2-methoxyphenyl)-3,5-pyridine dicarboxylate Using the procedure of Example 1, this product was obtained from diethyl 1,4-dihydro-4-(2-methoxyphenyl)-2,6-dimethyl-3,5-pyridine dicarboxylate and N-(2-methoxyphenyl)benzimidoyl chloride (5.2 g, 18.2%).

EXAMPLE 12

Diethyl 14,-dihydro-1-[N-(2-methoxyphenyl)benzimidoyl]-2,6-dimethyl-4-(4-(4-pyridyl)-3,5-pyridine dicarboxylate Using the procedure of Example 1, this product was obtained from diethyl 1,4-dihydro-4-(4-pyridyl)-2,6-dimethyl-3,5-pyridine dicarboxylate and N-(2-methoxyphenyl)benzimidoyl chloride (3.3 g, 12.2%).

EXAMPLE 13

Diethyl 1,4-dihydro-1-[N-(2-methylphenyl)benzimidoyl]-2,6-dimethyl-4-(2-trifluoromethylphenyl)-3,5-pyridine dicarboxylate Using the procedure of Example 1, this product was obtained from diethyl 1,4-dihydro-4-(2-trifluoromethylphenyl)-2,6-dimethyl-3,5-pyridine dicarboxylate and N-(2-methylphenyl)benzimidoyl chloride (4.3 g., 11.6%).

EXAMPLE 14

Diethyl 1,4-dihydro-1-[N-(2-chlorophenyl)benzimidoyl]-2,6-dimethyl-4-(4-cyanophenyl)-3,5-pyridine dicarboxylate Using the procedure of Example 1, this product was obtained from diethyl 1,4-dihydro-4-(4-cyanophenyl)-2,6-dimethyl-3,5-pyridine dicarboxylate and N-(2-chlorophenyl)benzimidoyl chloride (3.9 g., 13.8%).

EXAMPLE 15

Diethyl 1,4-dihydro-1-[N-(2-methoxyphenyl)benzimidoyl]-2,6-dimethyl-4-(4-cyanophenyl)-3,5-pyridine dicarboxylate Using the procedure of Example 1, this product was obtained from diethyl 1,4-dihydro-4-(4-cyanophenyl)-2,6-dimethyl-3,5-pyridine dicarboxylate and N-(2-methoxyphenyl)benzimidoyl chloride (2.6 g., 14.4%).

EXAMPLE 16

Diethyl 1,4-dihydro-1-(N-phenylbenzimidoyl)-2,6-dimethyl-4-(2-methylphenyl)-3,5-pyridine dicarboxylate Using the procedure of Example 1, this product was obtained from diethyl 1,4-dihydro-4-(2-methylphenyl)-2,6-dimethyl-3,5-pyridine dicarboxylate and N-phenylbenzimidoyl chloride (8.0 g., 33.6%).

EXAMPLE 17

Diethyl 1,4-dihydro-1-[N-(2-methylphenyl)benzimidoyl]-2,6-dimethyl-4-(4-cyanophenyl)-3,5-pyridine dicarboxylate Using the procedure of Example 1, this product was obtained from diethyl 1,4-dihydro-4-(4-cyanophenyl)-2,6-dimethyl-3,5-pyridine dicarboxylate and N-(2-methylphenyl)benzimidoyl chloride (3.7 g., 27.0%).

EXAMPLE 18

Diethyl 1,4-dihydro-1-(N-phenylbenzimidoyl)-2,6-dimethyl-4-(2-chlorophenyl)-3,5-pyridine dicarboxylate From the procedure of Example 1, this product was obtained from diethyl 1,4-dihydro-4-(2-chlorophenyl)-2,6-dimethyl-3,5-pyridine dicarboxylate and N-phenylbenzimidoyl chloride (7.8 g., 28.0%).

EXAMPLE 19

Diethyl 1,4-dihydro-1-(N-phenylbenzimidoyl)-2,6-dimethyl-4-(2-nitrophenyl)-3,5-pyridine dicarboxylate Using the procedure of Example 1, this product was obtained from diethyl 1,4-dihydro-4-(2-nitrophenyl)-2,6-dimethyl-3,5-pyridine dicarboxylate and N-phenylbenzimidoyl chloride (0.6 g., 3.9%).

What is claimed is:

1. An antihypertensive compound of the formula:

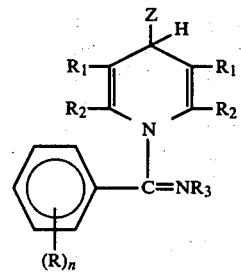

wherein,
Z is

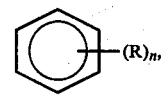

cycloalkyl, or pyridyl wherein R and 'n' are as defined herein;

each R is independently hydrogen, alkyl, alkenyl, alkynyl, cycloalkyl, aryl, aralkyl, sulfonamido, halogen, alkoxy, alkenyloxy, alkynyloxy, cyano, hydroxy, acyloxy, nitro, amino, alkylmercapto, alkylamino, alkanoylamino, carbalkoxyamino, carboxy, methanesulfonyl, carbalkoxy or trifluoromethyl;

each $R_1$ is cyano or $COR_4$ wherein $R_4$ is hydroxy, alkoxy, alkyl, alkenyl, alkynyl, alkylamino, amino, cycloalkyl, or alkoxyalkoxy;

each $R_2$ and $R_3$ is alkyl, alkenyl, alkynyl, cycloalkyl, pyridyl or

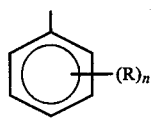

wherein R and "n" are as defined herein;
and n=0—3 wherein in Z, R, $R_1$, $R_2$ and $R_3$ the hydrocarbyl radical contains up to 7 carbon atoms when it is alkyl, alkenyl, alkynyl or cycloalkyl and up to 10 carbon atoms when aryl;

and acid addition salts thereof.

2. Diethyl 1,4-dihydro-1-(N-isobutyl benzimidoyl)-2,6-dimethyl-4-(2-trifluoromethylphenyl)-3,5-pyridine dicarboxylate.

3. Diethyl-1,4-dihydro-1-(N-cyclohexyl benzimidoyl)-2,6-dimethyl-4-(2-trifluoromethylphenyl)-3,5-pyridine dicarboxylate.

4. Diethyl-1,4-dihydro-1-N-ethyl benzimidoyl)-2,6-dimethyl-4-(2-trifluoromethylphenyl)-3,5-pyridine dicarboxylate.

5. Diethyl-1,4-dihydro-1-[N-(4-fluorophenyl)benzimidoyl]-2,6-dimethyl-4-(2-trifluoromethylphenyl)-3,5-pyridine dicarboxylate.

6. Diethyl-1,4-dihydro-1-(N-propyl benzimidoyl)-2,6-dimethyl-4-(2-trifluoromethylphenyl)-3,5-pyridine dicarboxylate.

7. Diethyl-1,4-dihydro-1-(N-neopentyl benzimidoyl)-2,6-dimethyl-4-(2-trifluoromethylphenyl)-3,5-pyridine dicarboxylate.

8. Diethyl-1,4-dihydro-1-(N-phenyl benzimidoyl)-2,6-dimethyl-4-(2-trifluoromethylphenyl)-3,5-pyridine dicarboxylate.

9. Diethyl-1,4-dihydro-1-(N-methyl benzimidoyl)-2,6-dimethyl-4-(2-trifluoromethylphenyl)-3,5-pyridine dicarboxylate.

10. Diethyl-1,4-dihydro-1-[N-(2-trifluoromethylphenyl)benzimidoyl]-2,6-dimethyl-4-(2-trifluoromethylphenyl)-3,5-pyridine dicarboxylate.

11. Diethyl-1,4-dihydro-1-[N-(2-methoxyphenyl)benzimidoyl]-2,6-dimethyl-4-(2-methoxyphenyl)-3,5-pyridine dicarboxylate.

12. Diethyl-1,4-dihydro-1-[N-(2-methoxyphenyl)benzimodyl]-2,6-dimethyl-4-(4-pyridyl)-3,5-pyridine dicarboxylate.

13. Diethyl-1,4-dihydro-1-[N-(2-methylphenylbenzimidoyl]-2,6-dimethyl-4-[2-trifluoromethylphenyl)-3,5-pyridine dicarboxylate.

14. Diethyl-1,4-dihydro-1-[N-(2-chlorophenyl)benzimidoyl]-2,6-dimethyl-4-(2-trifluoromethylphenyl)-3,5-pyridine dicarboxylate.

15. Diethyl-1,4-dihydro-1-[N-(2-methoxyphenyl)benzimidoyl]-2,6-dimethyl-4-(4-cyanophenyl)-3,5-pyridine dicarboxylate.

16. Diethyl-1,4-dihydro-1-(N-phenyl benzimidoyl)-2,6-dimethyl-4-(2-methylphenyl)-3,5-pyridine dicarboxylate.

17. Diethyl-1,4-dihydro-1-[N-(2-methylphenyl)benzimidoyl]-2,6-dimethyl-4-(4-cyanophenyl)-3,5-pyridine dicarboxylate.

18. Diethyl-1,4-dihydro-1-(N-phenyl benzimidoyl)-2,6-dimethyl-4-(2-chlorophenyl)-3,5-pyridine dicarboxylate.

19. Diethyl-1,4-dihydro-1-(N-phenyl benzimidoyl)-2,6-dimethyl-4-(2-nitrophenyl)-3,5-pyridine dicarboxylate.

* * * * *

UNITED STATES PATENT AND TRADEMARK OFFICE
CERTIFICATE OF CORRECTION

PATENT NO. : 4,302,591

DATED : November 24, 1981

INVENTOR(S) : James R. Shroff and Bernard Loev

It is certified that error appears in the above-identified patent and that said Letters Patent is hereby corrected as shown below:

ON THE TITLE PAGE,

In the Abstract, the formula:

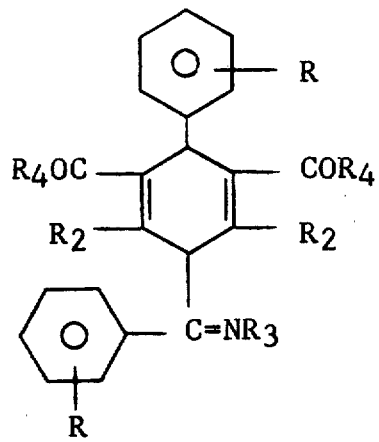

should have been written:

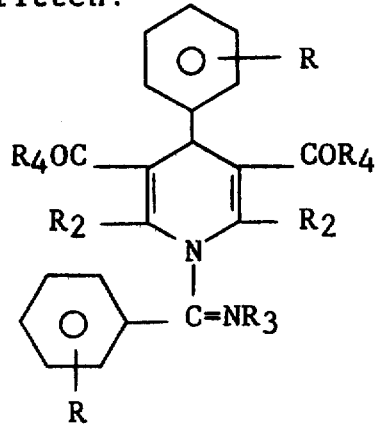

UNITED STATES PATENT AND TRADEMARK OFFICE
CERTIFICATE OF CORRECTION

PATENT NO. : 4,302,591

DATED : November 24, 1981

INVENTOR(S) : James R. Shroff and Bernard Loev

It is certified that error appears in the above-identified patent and that said Letters Patent is hereby corrected as shown below:

In the SPECIFICATION, column 2, lines 48 - 61, the formula:

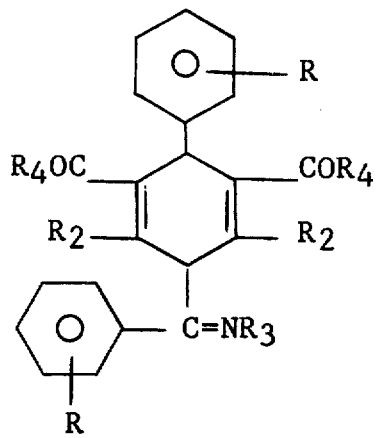

should have been written:

UNITED STATES PATENT AND TRADEMARK OFFICE
CERTIFICATE OF CORRECTION

PATENT NO. : 4,302,591  PAGE 3 of 3
DATED : November 24, 1981
INVENTOR(S) : James R. Shroff and Bernard Loev It is certified that error appears in the above-identified patent and that said Letters Patent is hereby corrected as shown below:

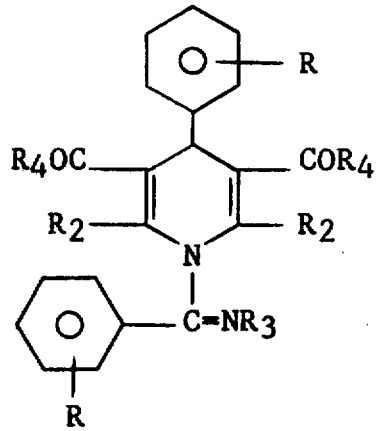

Signed and Sealed this

Twenty-ninth  Day of March 1983

[SEAL]

*Attest:*

GERALD J. MOSSINGHOFF

*Attesting Officer*   *Commissioner of Patents and Trademarks*